（12） United States Patent
Perrone et al.

(10) Patent No.: US 12,152,056 B2
(45) Date of Patent: Nov. 26, 2024

(54) METHOD AND CHROMATOGRAPHY SYSTEM FOR DETERMINING AMOUNT AND PURITY OF A MULTIMERIC PROTEIN

(71) Applicant: Regeneron Pharmaceuticals, Inc., Tarrytown, NY (US)

(72) Inventors: Michael Perrone, Brookfield, CT (US); Audrey Rodriguez, New York, NY (US); Andrew Tustian, Millwood, NY (US); Hanne Bak, New York, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 1005 days.

(21) Appl. No.: 16/542,766

(22) Filed: Aug. 16, 2019

(65) Prior Publication Data

US 2020/0055894 A1    Feb. 20, 2020

Related U.S. Application Data

(60) Provisional application No. 62/719,323, filed on Aug. 17, 2018.

(51) Int. Cl.
| | |
|---|---|
| *C07K 1/16* | (2006.01) |
| *C07K 1/00* | (2006.01) |
| *C07K 1/22* | (2006.01) |
| *C07K 1/36* | (2006.01) |
| *C07K 16/00* | (2006.01) |

(Continued)

(52) U.S. Cl.
CPC ............... *C07K 1/36* (2013.01); *C07K 1/00* (2013.01); *C07K 1/16* (2013.01); *C07K 1/22* (2013.01); *C07K 16/00* (2013.01); *G01N 30/14* (2013.01); *G01N 30/72* (2013.01); *G01N 30/8624* (2013.01); *G01N 33/6854* (2013.01);

(Continued)

(58) Field of Classification Search
CPC .......... G01N 33/6854; G01N 30/8624; G01N 30/14; G01N 30/72; G01N 30/00; G01N 2030/027; C07K 1/00; C07K 1/36; C07K 1/22; C07K 16/00; C07K 1/16; C07K 2317/31

See application file for complete search history.

(56) References Cited

U.S. PATENT DOCUMENTS

2021/0382065 A1\* 12/2021 Perrone .................... C07K 1/36

FOREIGN PATENT DOCUMENTS

| EP | 2500073 A1 | 9/2012 | |
|---|---|---|---|
| EP | 3172221 A2 \* | 5/2017 | ......... B01D 15/3819 |

(Continued)

OTHER PUBLICATIONS

Tustian et al. Development of purification processes for fully human bispecific antibodies based upon modification of protein A binding avidity. MABS 2016, vol. 8, No. 4, pp. 828-838 (Year: 2016).\*

(Continued)

*Primary Examiner* — Shafiqul Haq
(74) *Attorney, Agent, or Firm* — Troutman Pepper Hamilton Sanders LLP

(57) ABSTRACT

The invention relates to a chromatography system and method for assessing amount and/or purity of a multimeric (Continued)

protein in a sample, wherein the chromatography system comprises two different affinity chromatography matrices connected via a switch valve.

6 Claims, 9 Drawing Sheets

(51) Int. Cl.
    *G01N 30/14*     (2006.01)
    *G01N 30/72*     (2006.01)
    *G01N 30/86*     (2006.01)
    *G01N 33/68*     (2006.01)
    *G01N 30/00*     (2006.01)
    *G01N 30/02*     (2006.01)

(52) U.S. Cl.
    CPC .......... *C07K 2317/31* (2013.01); *G01N 30/00* (2013.01); *G01N 2030/027* (2013.01)

(56) References Cited

FOREIGN PATENT DOCUMENTS

| | | |
|---|---|---|
| JP | 2015-052533 A | 3/2015 |
| WO | 2012/057676 A1 | 5/2012 |
| WO | 2013/159858 A1 | 10/2013 |
| WO | 2016018740 A2 | 2/2016 |
| WO | WO-2017134440 A2 * | 8/2017 ........... A61K 39/395 |

OTHER PUBLICATIONS

Communication (International Search Report) issued in PCT/US2019/046769, mailed on Nov. 22, 2019, 9 pages.
Communication (Written Opinion) issued in PCT/US2019/046769, mailed on Nov. 22, 2019, 12 pages.
Tustian, A.D. et al., "Development of a Novel Affinity Chromatography Resin for Platform Purification of Bispecific Antibodies with Modified Protein a Binding Avidity" Biotechnology Progress (2018) vol. 34, No. 3, pp. 650-658.
Tustian, A.D. et al., "Development of Purification Processes for Fully Human Bispecific Antibodies Based Upon Modification of Protein A Binding Avidity" MADS (2016) vol. 9, No. 4, pp. 828-838.
Veritas, "In immunoprecipitation with Dynabeads Protein A or Dynabeads Protein G, what are the sites of dissociation when eluting under low pH conditions?", "Technical document, FAQ", [online], 2004-2020, [Searched on Jul. 31, 2023], On the Internet, <URL: https://www.veritastk.co.jp/products/reference/faq/Faq2_663.html> (Document showing well-known techniques).
Thermofisher Scientific, "Summary of optimisation of binding and elution conditions in affinity purification", "Related to molecular biology experiments", [online], May 30, 2016, [Searched on Jul. 31, 2023], On the Internet, <URL: https://www.thermofisher.com/blog/learning-at-the-bench/optimization-of-affinity-purification/> (Document showing well-known techniques).

* cited by examiner

METHOD AND CHROMATOGRAPHY SYSTEM FOR DETERMINING AMOUNT AND PURITY OF A MULTIMERIC PROTEIN

CROSS-REFERENCE TO RELATED APPLICATIONS

This application claims priority to U.S. Provisional Patent Application No. 62/719,323, filed Aug. 17, 2018, the disclosure of which is herein incorporated by reference in its entirety.

FIELD OF INVENTION

The present invention relates to a chromatography system and method for assessing an amount and/or purity of a multimeric protein in a sample, wherein the chromatography system comprises two different affinity chromatography matrices connected via a switch valve.

BACKGROUND

Bispecific antibodies are antibodies that can simultaneously and selectively bind to two different types of epitopes on the same or different antigens. The binding of multiple targets with a single molecule is an attractive therapeutic concept, especially in the fields of oncology and autoimmune disease. The most widely used application is in cancer immunotherapy, where bispecific antibodies are engineered to simultaneously bind a cytotoxic cell and a target such as a tumor cell to be destroyed. Additionally, targeting more than one molecule can be useful to circumvent the regulation of parallel pathways and avoid resistance to the treatment. Binding or blocking multiple targets in a pathway can be beneficial to stopping disease, as most conditions have complicated multifaceted effects throughout the body.

Multiple bispecific antibody formats have been proposed and are currently under development. One such format is based upon a standard fully human IgG antibody having an improved pharmacokinetic profile and minimal immunogenicity (see U.S. Pat. No. 8,586,713, and WO2016/018740), shown schematically in FIG. 1. A single common light chain and two distinct heavy chains combine to form such bispecific. One of the heavy chains contains a substituted Fc sequence (hereinafter "Fc*") that greatly reduces binding of the Fc* to Protein A due to H435R/Y436F (by EU numbering system; H95R/Y96F by IMGT exon numbering system) substitutions in the CH3 domain. As a result of co-expression of the Fc* and Fc heavy chains and the common light chain, three products are created: two of which (FcFc and Fc*Fc*) are homodimeric with respect to the heavy chains, and one of which (FcFc*) is the desired heterodimeric bispecific product. The Fc* sequence allows selective purification of the FcFc* bispecific product on commercially available affinity chromatography columns, due to intermediate binding affinity for Fc-binding proteins, such as Protein A, compared to the high affinity FcFc heavy chain homodimer, or the weakly binding Fc*Fc* homodimer.

Another antibody format is a so-called "one-arm" antibody described in WO2013/166604, shown schematically in FIG. 2A. This heterodimeric antibody consists, e.g., of two distinct heavy chains and only one light chain. In one such example, the heavy chain coupled to the light chain contains an Fc* sequence, while the heavy chain without a light chain contains the regular Fc sequence. The initial reaction mixture thus contains three products, two homodimeric (FcFc and Fc*Fc*) and the desired heterodimeric FcFc* product, which can be separated using affinity chromatography.

Yet another possible antibody format is an antibody construct with a C-terminal single-chain variable fragment (ScFv), shown schematically in FIG. 2B. These antibodies may be monospecific or bispecific, and comprise a single common light chain and two distinct heavy chains. In one example, one of the heavy chain has the Fc* sequence and is coupled to a ScFv, while the other heavy chain has the native Fc sequence and no ScFv. In another example, the heavy chain with the ScFv construct has the native Fc sequence, and the Fc* heavy chain does not have ScFv. Additional examples, where an additional mutation that abrogates binding to Affinity Columns is a mutation to the Heavy chain Variable Region (VH) on the same chain with the Fc* mutation, are provided in e.g. U.S. Pat. No. 9,493,563 (mutations in VH3 and Fc described as IMGT 3, 5, 7, 20, 22, 26, 27, 79, 81, 84, 84.2, 85.1, 86, 90), which is incorporated by reference in its entirety. As in the above examples, the three-component mixture of FcFc* heterodimer and the FcFc and Fc*Fc* homodimers can be separated using the differential binding affinity chromatography.

There is a need in the field of commercial scale production of bispecific antibodies to assess the relative and absolute amount and purity of the heterodimer in various stages of antibody production and purification. For this, effective resolution between the heterodimer, and the two homodimer impurities is desired. Moreover, speed and efficiency of quality control measurements are desired during the cell culture process as well as the purification process of antibodies. The present invention addresses this and other needs by providing a novel chromatography system and method.

The foregoing discussion is presented solely to provide a better understanding of nature of the problems confronting the art and should not be construed in any way as an admission as to prior art nor should the citation of any reference herein be construed as an admission that such reference constitutes "prior art" to the instant application.

SUMMARY OF THE INVENTION

Various non-limiting aspects and embodiments of the invention are described below.

The present invention describes a novel chromatography system comprising a switch valve and a method of quantitatively assessing the amount and/or purity of the heterodimer fraction in a sample.

In one aspect, the present invention provides a method for quantifying an amount and/or purity of a protein in a sample comprising a mixture of the protein, a first protein impurity, and a second protein impurity, wherein the protein and the first impurity bind to a first affinity matrix and the second impurity does not substantially bind to the first affinity matrix and binds to a second affinity matrix, said method comprising the steps of:
  a. applying the sample to a chromatography system comprising the first affinity matrix, the second affinity matrix, and a detector, wherein the first affinity matrix is serially connected to the second affinity matrix via a switch valve;
  b. eluting the second impurity from the first affinity matrix onto the second affinity matrix under a first set of conditions;
  c. switching the switch valve to bypass the second affinity matrix, eluting the protein through the detector under a second set of conditions, and determining the amount of the eluted protein;

d. eluting the first impurity through the detector under a third set of conditions and determining the amount of the eluted first impurity;

e. eluting the second impurity from the second affinity matrix through the detector under the third set of conditions, and determining the amount of the eluted second impurity, and f. quantifying the amount and/or purity of the protein in the sample.

In one embodiment the protein is a multimeric protein, e.g. an antibody. In one embodiment, the protein is an antibody of interest, and the first and second protein impurities are multimeric proteins, e.g., antibodies that may or may not be structurally related to the antibody of interest. In one embodiment, the protein is a bispecific antibody, i.e., a heterodimeric protein, the first protein impurity is a first homodimeric protein, and the second protein impurity is a second homodimeric protein. In some cases, the mixture of multimeric proteins is produced by a plurality of eukaryotic cells, such as, for example, Chinese hamster ovary (CHO) cells in a cell culture.

In one embodiment, the protein has a lower affinity to the first affinity matrix than the first impurity. In one embodiment the protein is a heterodimeric protein, the first protein impurity is a first homodimeric protein, and the second protein impurity is a second homodimeric protein, the heterodimeric protein and the first homodimeric protein bind to the first affinity matrix and the second homodimeric protein does not substantially bind to the first affinity matrix and binds to the second affinity matrix.

In one embodiment, the protein comprises a first immunoglobulin CH3 domain and a second immunoglobulin CH3 domain, wherein said first and second immunoglobulin CH3 domains are different in their affinity to the first affinity matrix, and wherein the sample comprises a mixture comprising said protein, a protein comprising two first CH3 domains, and a protein comprising two second CH3 domains.

In one embodiment, the second CH3 domain comprises H435R and Y436F (by EU numbering system; H95R/Y96F by IMGT exon numbering system) amino acid substitutions. In another embodiment, the second CH3 domain comprises an H435R (by EU numbering system; H95R by IMGT exon numbering system) amino acid substitution. In some embodiments, the second CH3 domain comprising an H435R (by EU numbering system; H95R by IMGT exon numbering system) amino acid substitution and exhibits weak or no detectable binding to Fc-binding ligands, such as protein A, protein G, protein L, or derivatives thereof.

In one embodiment, the protein is an antibody. In one embodiment, the protein is a bispecific antibody.

In one embodiment, the first affinity matrix comprises protein A and the second affinity matrix comprises protein G.

In one embodiment, the first set of conditions comprises a first pH, the second set of conditions comprises a second pH, and the third set of conditions comprises a third pH. In one embodiment, the second pH is lower than the first pH, and the third pH is lower than the second pH. In one embodiment, the first pH is from about pH 5.0 to about pH 7.4, the second pH is from about pH 4.3 to about pH 5.6, and the third pH is from about pH 2.0 to about pH 2.8.

In one embodiment, the first set of conditions, the second set of conditions, and the third set of conditions comprise a mobile phase modifier. In one embodiment, the mobile phase modifier is a salt buffer selected from LiCl, NaCl, KCl, $MgCl_2$, and $CaCl_2$ buffer.

In another aspect, a method for quantifying an amount and/or purity of a heterodimeric protein in a sample is provided, comprising a mixture of the heterodimeric protein, a first homodimeric protein, and a second homodimeric protein, wherein the heterodimeric protein and the first homodimeric protein bind to a first affinity matrix and the second homodimeric protein does not substantially bind to the first affinity matrix and binds to a second affinity matrix, said method comprising the steps of:

a. applying the sample to a chromatography system comprising the first affinity matrix, the second affinity matrix, and a detector, wherein the first affinity matrix is serially connected to the second affinity matrix via a switch valve;

b. eluting the second homodimeric protein from the first affinity matrix onto the second affinity matrix under a first set of conditions;

c. switching the switch valve to bypass the second affinity matrix, eluting the heterodimeric protein through the detector under a second set of conditions, and determining the amount of the eluted protein;

d. eluting the first homodimeric protein through the detector under a third set of conditions and determining the amount of the eluted first impurity;

e. eluting the second homodimeric protein from the second affinity matrix through the detector under the third set of conditions, and determining the amount of the eluted second impurity, and f. quantifying the amount and/or purity of the protein in the sample.

In still another aspect, a method for quantifying an amount and/or purity of a heterodimeric protein in a sample is provided, comprising a mixture of the heterodimeric protein, a first homodimeric protein, and a second homodimeric protein, wherein the heterodimeric protein and the first homodimeric protein bind to a protein A matrix and the second homodimeric protein does not substantially bind to the protein A matrix and binds to a protein G matrix, said method comprising the steps of:

a. applying the sample to a chromatography system comprising the protein A matrix, the protein G matrix, and a detector, wherein the protein A matrix is serially connected to the protein G matrix via a switch valve;

b. eluting the second homodimeric protein from the protein A matrix onto the protein G matrix under a first set of conditions;

c. switching the switch valve to bypass the protein G matrix, eluting the heterodimeric protein through the detector under a second set of conditions, and determining the amount of the eluted protein;

d. eluting the first homodimeric protein through the detector under a third set of conditions and determining the amount of the eluted first impurity;

e. eluting the second homodimeric protein from the protein G affinity matrix through the detector under the third set of conditions, and determining the amount of the eluted second impurity, and f. quantifying the amount and/or purity of the protein in the sample.

In one embodiment, the heterodimeric protein comprises FcFc*, the first homodimeric protein comprises FcFc, and the second homodimeric protein comprises Fc*Fc*.

In another aspect, a chromatography system comprising a first affinity matrix, a second affinity matrix, and a detector is provided, wherein each of the first affinity matrix, the second affinity matrix and the detector are connected via a switch valve.

In another aspect, a chromatography system is provided comprising (i) a protein A chromatography column, (ii) a protein G chromatography column, and (iii) a detector comprising an HPLC column equipped with a UV detector, a charge aerosol detector, and/or a mass-spectrometer, wherein each of the protein A chromatography column, the protein G chromatography column and to the detector are connected via a switch valve.

These and other aspects of the present invention will become apparent to those skilled in the art after a reading of the following detailed description of the invention, including the appended claims.

BRIEF DESCRIPTION OF THE DRAWINGS

FIG. 2(A) shows a heterodimeric "one-arm" antibody, which consists of two distinct heavy chains and only one light chain, where one heavy chain does not contain a Fab fragment (e.g. contains only the heavy chain constant domain). FIG. 2(B) shows two exemplary antibody constructs with a C-terminal single-chain variable fragment (ScFv). The Fc* mutation may be incorporated into either the first or the second heavy chain (constant domain) polypeptide.

DETAILED DESCRIPTION

Figure 1:
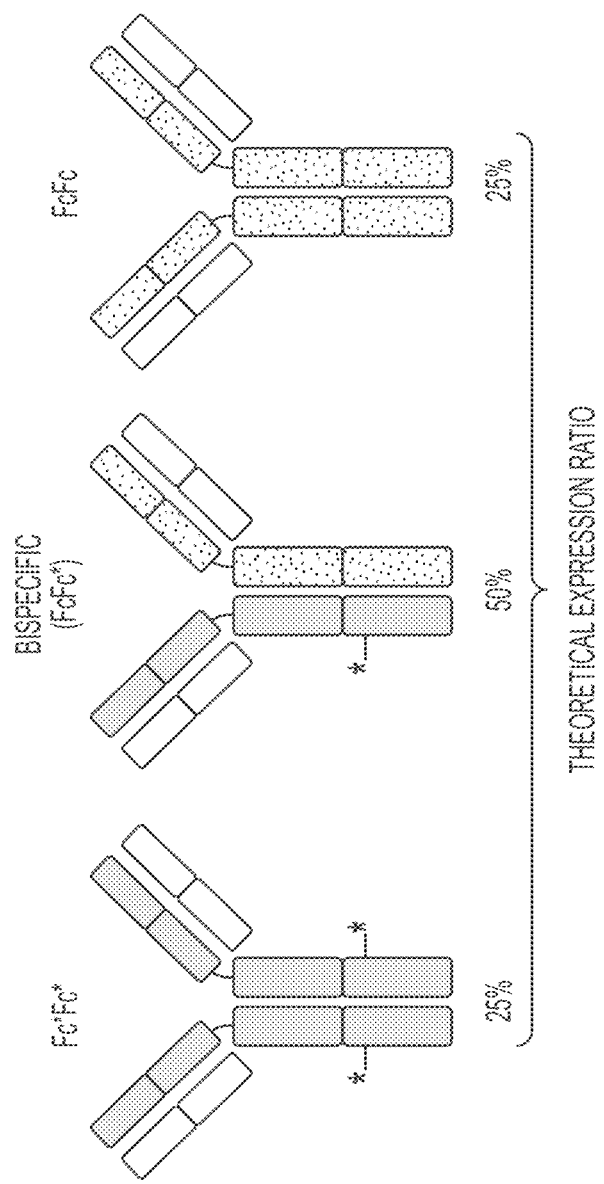
FIG. 1 is a schematic representation of a bispecific antibody format suitable for separating with the method of the invention based upon a standard fully human IgG antibody having single common light chain and two distinct heavy chains, one comprising an Fc* mutation and one with a native (Fc) sequence. Note one representative example is drawn, and that the Fc* mutation may be incorporated into either the first or the second heavy chain.
Figure 2A:
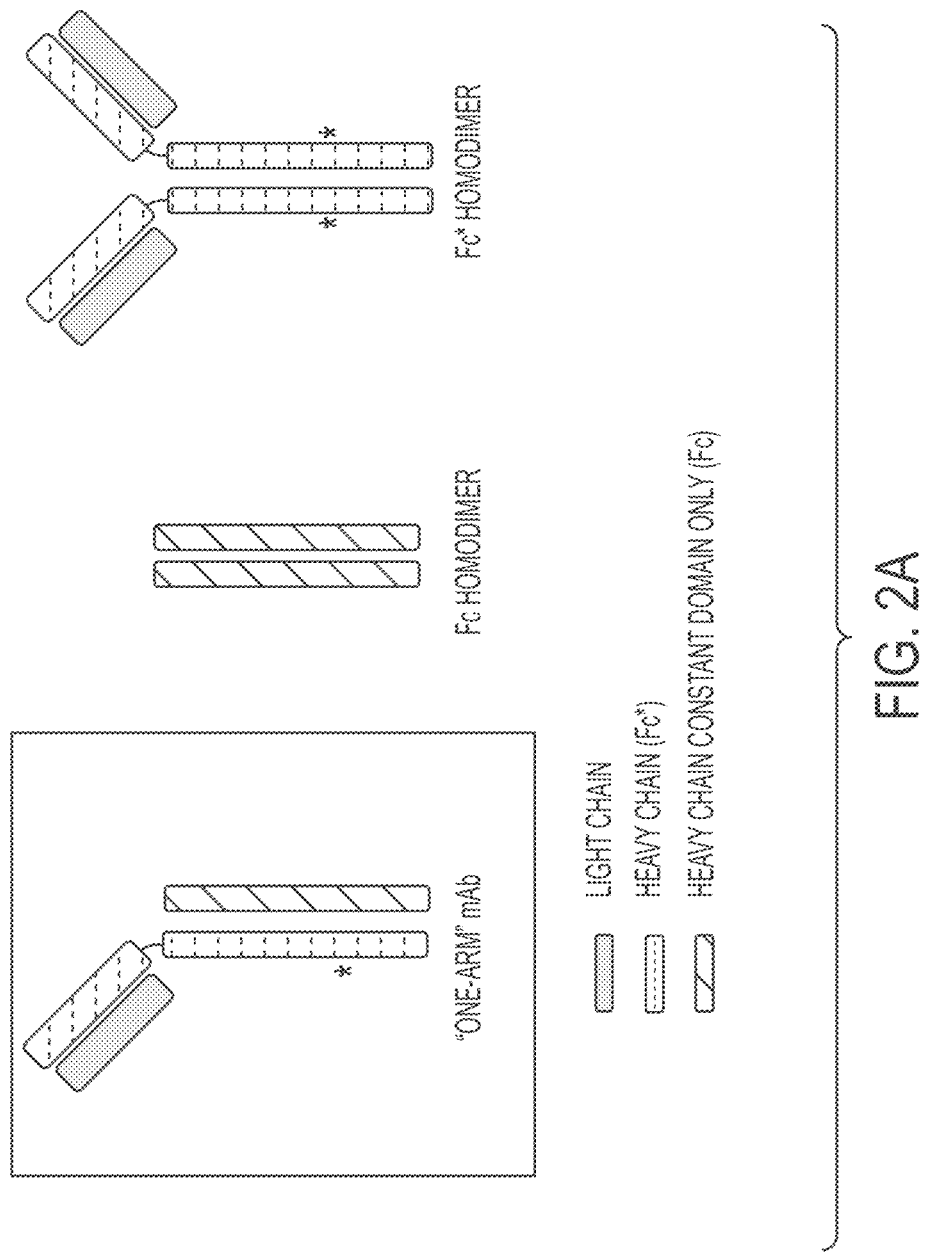
FIGS. 2A and 2B show schematic representations of two additional antibody formats suitable for separation according to embodiments of the invention.
Figure 2B:
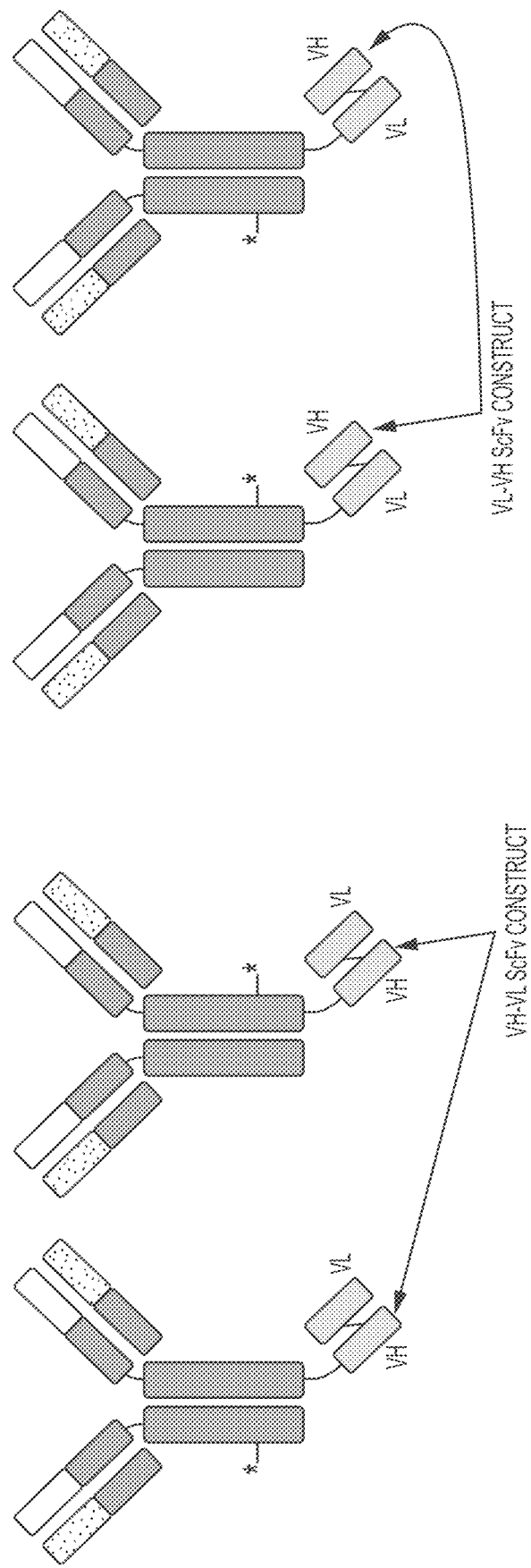
Figure 3:
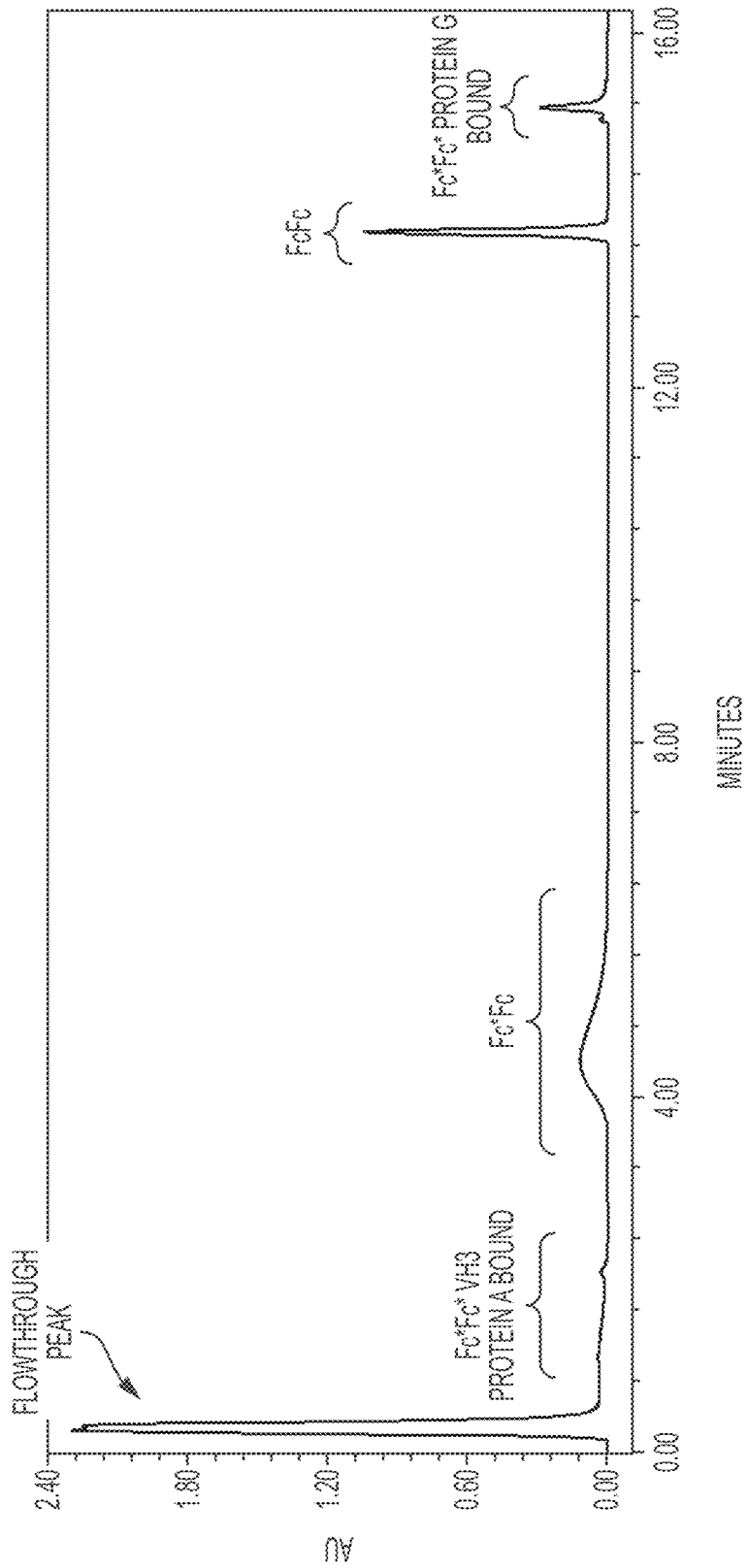
FIG. 3 depicts a titer chromatogram illustrating separation of a mixture of a bispecific antibody and monomeric impurities according to the method of the disclosure and utilizing the system according to an embodiment of the disclosure.

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Therefore, specific structural and functional details disclosed herein are not to be interpreted as limiting, but merely as a representative basis for teaching one skilled in the art to variously employ the present invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, particular methods and materials are now described.

As used in this specification and the appended claims, the singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure.

Not-limiting examples of proteins suitable for separation with methods according to the invention may include, without limitation, heterodimeric antibodies, e.g., bispecific antibodies, one-arm antibodies, and ScFv antibodies. Bispecific antibodies generally comprise two different heavy chains, with each heavy chain specifically binding a different epitope—either on two different molecules (e.g., two different antigens or an antigen and a T-cell receptor) or on the same molecule (e.g., on the same antigen). If a bispecific antibody is capable of selectively binding two different epitopes (a first epitope and a second epitope), the affinity of the first heavy chain for the first epitope will generally be at least one to two or three or four orders of magnitude lower than the affinity of the first heavy chain for the second epitope, and vice versa. The epitopes recognized by the bispecific antibody can be on the same or a different target (e.g., on the same or a different protein). Bispecific antibodies can be made, for example, by combining heavy chains that recognize different epitopes of the same antigen. For example, nucleic acid sequences encoding heavy chain variable sequences that recognize different epitopes of the same antigen can be fused to nucleic acid sequences encoding different heavy chain constant regions, and such sequences can be expressed in a cell that expresses an immunoglobulin light chain. A typical bispecific antibody has two heavy chains each having three heavy chain CDRs, followed by (N-terminal to C-terminal) a CH1 domain, a hinge, a CH2 domain, and a CH3 domain, and an immunoglobulin light chain that either does not confer antigen-binding specificity but that can associate with each heavy chain, or that can associate with each heavy chain and that can bind one or more of the epitopes bound by the heavy chain antigen-binding regions, or that can associate with each heavy chain and enable binding or one or both of the heavy chains to one or both epitopes.

The phrase "Fc-containing protein" includes antibodies, bispecific antibodies, immunoadhesins, and other binding proteins that comprise at least a functional portion of an immunoglobulin CH2 and CH3 region. A "functional portion" refers to a CH2 and CH3 region that can bind a Fc receptor (e.g., an FcγR; or an FcRn, i.e., a neonatal Fc receptor), and/or that can participate in the activation of complement. If the CH2 and CH3 region contains deletions, substitutions, and/or insertions or other modifications that render it unable to bind any Fc receptor and also unable to activate complement, the CH2 and CH3 region is not functional.

Fc-containing proteins can comprise modifications in immunoglobulin domains, including where the modifications affect one or more effector function of the binding protein (e.g., modifications that affect FcγR binding, FcRn binding and thus half-life, and/or CDC activity). Such modifications include, but are not limited to, the following modifications and combinations thereof, with reference to EU numbering of an immunoglobulin constant region: 238, 239, 248, 249, 250, 252, 254, 255, 256, 258, 265, 267, 268, 269, 270, 272, 276, 278, 280, 283, 285, 286, 289, 290, 292, 293, 294, 295, 296, 297, 298, 301, 303, 305, 307, 308, 309, 311, 312, 315, 318, 320, 322, 324, 326, 327, 328, 329, 330, 331, 332, 333, 334, 335, 337, 338, 339, 340, 342, 344, 356, 358, 359, 360, 361, 362, 373, 375, 376, 378, 380, 382, 383, 384, 386, 388, 389, 398, 414, 416, 419, 428, 430, 433, 434, 435, 437, 438, and 439.

For example, and not by way of limitation, the binding protein is an Fc-containing protein and exhibits enhanced serum half-life (as compared with the same Fc-containing protein without the recited modification(s)) and have a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at 428 and/or 433 (e.g., L/R/SI/P/Q or K) and/or 434 (e.g., H/F or Y); or a modification at 250 and/or 428; or a modification at 307 or 308 (e.g., 308F, V308F), and 434. In another example, the modification can comprise a 428L (e.g., M428L) and 434S (e.g., N434S) modification; a 428L, 2591 (e.g., V2591), and a 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); a 307 and/or 308 modification (e.g., 308F or 308P).

The term "star substitution," "Fc*," and "HC*" includes any molecule, immunoglobulin heavy chain, Fc fragment, Fc-containing molecule and the like that contains a mutation that abrogates the binding to bacterial proteins known to bind the Fc domain of immunoglobulins, such as Protein A, Protein G, Protein L or derivatives thereof (see for example SpA and SpA mimetic affinity ligands described in Choe, W., et al. 2016, *Materials* 9, 994, doi:10.3390/ma9120994, which is incorporated herein by reference). Immunoglobulins or other Fc-containg proteins may, for example, contain a modified sequence within the CH3 domain that greatly reduces binding to Protein A, as described, e.g., in WO2016/018740 and U.S. Pat. No. 8,586,713. A mutation in the Fc domain may be designated as the "star substitution" or Fc* throughout the specification for ease of noting that one polypeptide of a dimer contains a mutation, and one does not. Thus, Fc*Fc* denotes a homodimer wherein both monomers comprise an Fc*, and FcFc*, or Fc*Fc, denotes a heterodimer with respect to the Fc* substitution. The terms FcFc* and Fc*Fc are used interchangeably herein.

The phrase "mobile phase modifier" includes moieties that reduce the effect of, or disrupt, non-specific (i.e., non-affinity) ionic and other non-covalent interactions between proteins. "Mobile phase modifiers" include, for example, salts, ionic combinations of Group I and Group II metals with acetate, bicarbonate, carbonate, a halogen (e.g., chloride or fluoride), nitrate, phosphate, or sulfate. A non-limiting illustrative list of "mobile phase modifiers" includes beryllium, lithium, sodium, and potassium salts of acetate; sodium and potassium bicarbonates; lithium, sodium, potassium, and cesium carbonates; lithium, sodium, potassium, cesium, and magnesium chlorides; sodium and potassium fluorides; sodium, potassium, and calcium nitrates; sodium and potassium phosphates; and calcium and magnesium sulfates.

"Mobile phase modifiers" also include chaotropic agents, which weaken or otherwise interfere with non-covalent forces and increase entropy within biomolecular systems. Non-limiting examples of chaotropic agents include butanol, calcium chloride, ethanol, guanidinium chloride, lithium perchlorate, lithium acetate, magnesium chloride, phenol, propanol, sodium dodecyl sulfate, thiourea, and urea. Chaotropic agents include salts that affect the solubility of proteins. The more chaotropic anions include for example chloride, nitrate, bromide, chlorate, iodide, perchlorate, and thiocyanate. The more chaotropic cations include for example lithium, magnesium, calcium, and guanidinium.

"Mobile phase modifiers" include those moieties that affect ionic or other non-covalent interactions that, upon addition to a pH gradient or step, or upon equilibration of a Protein A support in a "mobile phase modifier" and application of a pH step or gradient, results in a broadening of pH unit distance between elution of a homodimeric IgG and a heterodimeric IgG (e.g., a wild-type human IgG and the same IgG but bearing one or more modifications of its CH3 domain as described herein). A suitable concentration of a "mobile phase modifier" can be determined by its concentration employing the same column, pH step or gradient, with increasing concentration of "mobile phase modifier" until a maximal pH distance is reached at a given pH step or pH gradient. "Mobile phase modifiers" may also include non-polar modifiers, including for example propylene glycol, ethylene glycol, and the like.

An affinity matrix is the solid support non-aqueous matrix onto which an affinity protein, e.g., Protein A, Protein G, Protein L, Protein Z, or recombinant derivatives thereof, adheres (Choe, W., et al, 2016 supra). Such supports include agarose, sepharose, glass, silica, polystyrene, nitrocellulose, charcoal, sand, cellulose and any other suitable material. Such materials are well known in the art. Any suitable method can be used to affix the second protein to the solid support. Methods for affixing proteins to suitable solid supports are well known in the art. See e.g. Ostrove, in Guide to Protein Purification, Methods in Enzymology, 182: 357-371, 1990. Such solid supports, with and without immobilized Protein A, are readily available from many commercial sources including such as Vector Laboratory (Burlingame, Calif.), Santa Cruz Biotechnology (Santa Cruz, Calif.), BioRad (Hercules, Calif.), Amersham Biosciences (part of GE Healthcare, Uppsala, Sweden), Pall (Port Washington, NY) and EMD-Millipore (Billerica, Mass.). Protein A immobilized to a pore glass matrix is commercially available as PROSEP®-A (Millipore). The solid phase may also be an agarose-based matrix. Protein A immobilized on an agarose matrix is commercially available as, e.g., MAB-SELECT™ (GE Amersham Biosciences). Affinity columns containing an immunoglobulin- or Fc-binding protein may be manufactured by affixing any of the SpA or mimetic SpA ligands to a solid support.

As used herein, "affinity chromatography" is a chromatographic method that makes use of the specific, reversible interactions between biomolecules rather than general properties of the biomolecule such as isoelectric point, hydrophobicity, or size, to effect chromatographic separation. "Protein A affinity chromatography" or "Protein A chromatography" refers to a specific affinity chromatographic method that makes use of the affinity of the IgG binding domains of Protein A for the Fc portion of an immunoglobulin molecule. This Fc portion comprises human or animal immunoglobulin constant domains CH2 and CH3 or immunoglobulin domains substantially similar to these.

Protein A is a cell wall component produced by several strains of Staphylococcus aureus which consists of a single polypeptide chain. The Protein A gene product consists of five homologous repeats attached in a tandem fashion to the pathogen's cell wall. The five domains are approximately 58 amino acids in length and denoted EDABC, each exhibiting immunoglobulin binding activity (Tashiro M & Montelione G T (1995) Curr. Opin. Struct. Biol., 5(4): 471-481. The five homologous immunoglobulin binding domains fold into a three-helix bundle. Each domain is able to bind proteins from many mammalian species, most notably IgGs (Hober S et al., (2007) J. Chromatogr. B Analyt. Technol. Biomed. Life Sci., 848(1): 40-47). Protein A binds the heavy chain of most immunoglobulins within the Fc region but also within the Fab region in the case of the human VH3 family (Jansson B et al, (1998) FEMS Immunol. Med. Microbiol., 20(1): 69-78). Protein A binds IgG from various species including human, mouse, rabbit, and guinea pig but does not bind human IgG3 (Hober S et al., (2007) supra). The inability of human IgG3 to bind Protein A can be explained by the H435R and Y436F substitutions in the human IgG3 Fc region (EU numbering, Jendeberg et al., (1997) J. Immunol. Methods, 201(1): 25-34). Besides IgG, Protein A also interacts with IgM and IgA.

The capacity of Protein A to bind antibodies with such high affinity is the driving motivation for its industrial scale use in biologic pharmaceuticals. Protein A used for production of antibodies in bio-pharmaceuticals is usually produced recombinantly in E. coli and functions essentially the same as native Protein A (Liu H F et al., (2010) MAbs, 2(5): 480-499). Most commonly, recombinant Protein A is bound to a stationary phase chromatography resin for purification of antibodies. Optimal binding occurs at pH8.2, although binding is also good at neutral or physiological conditions (pH 7.0-7.6). Elution is usually achieved through pH shift towards acidic pH (glycine-HCl, pH2.5-3.0). This effectively dissociates most protein-protein and antibody-antigen binding interactions without permanently affecting protein structure. Nevertheless, some antibodies and proteins are damaged by low pH, and in some cases it may be best to neutralize immediately after recovery by addition of 1/10th volume of alkaline buffer such as 1 M Tris-HCl, pH 8.0 to minimize the duration of time in the low-pH condition.

There are various commercially available Protein A chromatography resins. The main differences between these media are the support matrix type, Protein A ligand modification, pore size and particle size. The differences in these factors give rise to differences in compressibility, chemical and physical robustness, diffusion resistance and binding capacity of the adsorbents (Hober S et al., (2007), supra). Examples of Protein A chromatography resins include but are not limited to the Mab Select SuRe™ Protein A resin and MabSelect™ Protein A resin from GE Healthcare, EconoPac Protein A column from BioRad, rProA, available from Applied Biosystems, and POROS® A from Thermo Fisher, as seen in the Examples.

Protein A, as used herein, encompasses native protein from the cell wall of Staphylococcus aureus, Protein A produced by recombinant or synthetic methods, and variants that retain the ability to bind to an Fc region. Engineered Protein A may be for example a Z-domain tetramer, a Y-domain tetramer, or an engineered Protein A that lacks D and E domains. These engineered Protein A exemplars are unable to bind (or bind with very low affinity if at all) to the VH3 domain of an immunoglobulin, but can still bind to the CH3 domains of IgG1, IgG2 and IgG4. In practice, Protein A chromatography involves using Protein A immobilized to a solid support. See Gagnon, Protein A Affinity Chromotography, Purification Tools for Monoclonal Antibodies, pp. 155-198, Validated Biosystems, 1996.

Protein G is a bacterial cell wall protein isolated from group C and G Streptococci. DNA sequencing of native Protein G isolated from different Streptococci identified immunoglobulin binding domains as well as sites for albumin and cell surface binding. Depending on the strain both the immunoglobulin binding region and the albumin binding region consist of 2-3 independently folding units (Tashiro M & Montelione G T (1995) Curr. Opin. Struct. Biol., 5(4): 471-481). Protein G from strain G148 consists of 3 albumin and immunoglobulin binding domains respectively denoted ABD1, ABD2, and ABD3, and C1, C2, and C3 (Olsson A et al., (1987) Eur. J. Biochem., 168(2): 319-324). Each immunoglobulin binding domain denoted C1, C2, and C3 is approximately 55 residues and separated by linkers of about 15 residues. All experimentally solved 3D structures of Protein G immunoglobulin binding domains show a highly compact globular structure without any disulfide bridges or tightly bound prosthetic groups (Sauer-Eriksson A E et al., (1995) Structure, 3(3): 265-278; Derrick J P & Wigley D B (1992) Nature, 359(6397): 752-754; Derrick J P & Wigley D B (1994) J. Mol. Biol., 243(5): 906-918; Lian L Y et al., (1994) Nat. Struct. Biol., 1(6): 355-357). The structure comprises a four-stranded beta-sheet made up of two antiparallel beta-hairpins connected by an alpha-helix.

Streptococcus strains from groups C and G show binding to all human subclasses of IgG including IgG3 in contrast to Protein A. Protein G also binds to several animal IgG including mouse, rabbit, and sheep (Bjorck L & Kronvall G (1984) J. Immunol., 133(2): 969-974; Akerstrom B et al., (1985) J. Immunol., 135(4): 2589-2592; Akerstrom B & Bjorck L (1986) J. Biol. Chem., 261(22): 10240-10247; Fahnestock S R et al., (1986) J. Bacteriol., 167(3): 870-880). Hence, Protein G exhibits a broader binding spectrum to subclasses of different species compared to Protein A. In addition, Protein G binds to the Fab portion of IgGs with high affinity. The structure of the binding domain of streptococcal Protein G has been determined both alone (by NMR, Lian L Y et al., (1994) supra), and in complex with an IgG1 Fab (by x-ray crystallography, Derrick J P & Wigley D B (1992) supra and Derrick J P & Wigley D B (1994) supra). All experimentally solved 3D structures showed a binding within the CH1 domain of IgG heavy chains.

The Protein G, as used herein, may be a naturally occurring or modified Streptococcal Protein G, or it may be an engineered Protein G. Engineered Protein G may comprise the B1 domain (aka GB1) and may be conjugated or unconjugated. In another embodiment, the second affinity matrix comprises a protein L ligand and its derivatives affixed to a solid substrate. Similarly to Protein A, recombinant Protein G produced in *E. coli* may be used to purify antibodies. The albumin and cell surface binding domains have been eliminated from recombinant Protein G to reduce non specific binding and, therefore, can be used to separate IgG from crude samples. Similarly to Protein A, recombinant Protein G is bound to a stationary phase chromatography resin for purification of antibodies. Optimal binding occurs at pH 5, although binding is also good at pH 7.0-7.2; as for Protein A, elution is also achieved through pH shift towards acidic pH (glycine-HCl, pH2.5-3.0). Examples of Protein G chromatography resins include but are not limited to the Protein G Sepharose™ 4 Fast Flow resin and HiTrap™ Protein G HP column from GE Healthcare.

Similarly to Protein A, recombinant Protein G produced in *E. coli* is routinely used to purify antibodies. The albumin and cell surface binding domains have been eliminated from recombinant Protein G to reduce nonspecific binding and, therefore, can be used to separate IgG from crude samples. Similarly to Protein A, recombinant Protein G is bound to a stationary phase chromatography resin for purification of antibodies. Optimal binding occurs at pH 5, although binding is also good at pH 7.0-7.2; as for Protein A, elution is also achieved through pH shift towards acidic pH (glycine-HCl, pH2.5-3.0). Examples of Protein G chromatography resins include but are not limited to the Protein G Sepharose™ 4 Fast Flow resin and HiTrap™ Protein G HP column from GE Healthcare, rProG, available from Applied Biosystems, and POROS® G from Thermo Fisher, as seen in the Examples.

Other proteins, such as Protein L, M1 Protein, and Protein H, may also be used in the affinity chromatography of the present invention. Protein L is an immunoglobulin binding protein that was originally derived from the bacteria Peptostreptococcus magnus, but is now produced recombinantly (Bjorck L (1988) J. Immunol., 140(4): 1194-1197; Kastern W et al., (1992) J. Biol. Chem., 267(18): 12820-12825). Protein L has the unique ability to bind through kappa light chain interactions without interfering with an antibody's antigen binding site (Nilson B H et al., (1993) J. Immunol. Methods, 164(1): 33-40). This gives Protein L the ability to bind a wider range of immunoglobulin classes and subclasses than other antibody binding protein. Protein L will bind to all classes of immunoglobulins (IgG, IgM, IgA, IgE and IgD). Protein L will also bind single chain variable fragments (scFv) and Fab fragments (Nilson B H et al., (1993) supra; Bottomley S P et al., (1995) Bioseparation, 5(6): 359-367). Protein L binds the human variable domains of kappa I, III, and IV subclasses and mouse kappa I subclass (Nilson B H et al., (1992) supra). Examples of Protein L chromatography resins include but are not limited to the Protein L resin from Genescript as used in examples.

M1 Protein and Protein H are surface proteins simultaneously present at the surface of certain strains of *Streptococcus pyogenes*. Protein H has affinity for the Fc region of IgG (Akesson P et al., (1990) Mol. Immunol., 27(6): 523-531; Akesson P et al., (1994) Biochem. J., 300 (Pt 3): 877-886). Protein H binds to the Fc region of IgGs from human, monkeys and rabbits (Akesson P et al., (1990), supra; Frick I M et al., (1995) EMBO J., 14(8): 1674-1679). M Proteins are also known to bind fibrinogen (Kantor F S (1965) J Exp Med, 121: 849-859), and previous work has demonstrated that M1 Protein from the API strain also has affinity for albumin and polyclonal IgG (Schmidt K H & Wadstrom T (1990) Zentralbl. Bakteriol., 273(2): 216-228).

Affinity chromatography also includes media that can be used to selectively bind and thus purify antibodies, fragments of antibodies, or chimeric fusion proteins that contain immunoglobulin domains and/or sequences. Antibodies include IgG, IgA, IgM, IgY, IgD and IgE types. Antibodies also include single chain antibodies such as camelid antibodies, engineered camelid antibodies, single chain antibodies, single-domain antibodies, nanobodies, and the like. Antibody fragments include VH, VL, CL, CH sequences. Antibody fragments and fusion proteins containing antibody sequences include for example F(ab')3, F(ab')2, Fab, Fc, Fv, dsFv, (scFv)2, scFv, scAb, minibody, diabody, triabody, tetrabody, Fc-fusion proteins, trap molecules, and the like (see Ayyar et al., Methods 56 (2012): 116-129). Such affinity chromatography media may contain ligands that selectively bind antibodies, their fragments, and fusion proteins contains those fragments. Such ligands include antibody binding proteins, bacterially derived receptors, antigens, lectins or anti-antibodies directed to the target molecule. The antibody requiring purification. For example, camelid-derived affinity ligands directed against any one or more of IgG-CH1, IgG-Fc, IgG-CH3, IgG1, LC-kappa, LC-lambda, IgG3/4, IgA, IgM, and the like may be used as affinity ligands (commercially available as CAPTURESELECT chromatography resins, Life Technologies, Inc., Carlsbad, Calif.).

Techniques that ease the recovery of heterodimers from homodimers based on a differential affinity of the heterodimers for an affinity reagent have been described. The first example of differential affinity technique involved the use of two different heavy chains from two different animal species, wherein one of which does not bind Protein A (Lindhofer H et al., (1995) J Immunol., 155(1): 219-225). The same authors also described the use of two different heavy chains originating from two different human immunoglobulin isotypes (IGHG1 and IGHG3), one of which does not bind Protein A (IGHG3; see U.S. Pat. No. 6,551,592 Lindhofer H et al.). A variation of the latter technique has been described in WO10/151792 (Davis S et al.) and involved the use of the two amino acid substitutions H435R/Y436F described by Jendeberg et at (Jendeberg et al., (1997) J. Immunol. Methods, 201(1): 25-34) to greatly reduce the affinity for Protein A in one of the heterodimer heavy chains.

As used herein, the term "detector" comprises a chromatography column equipped with a means for detecting and/or assessing components of a mixture being eluted off the chromatography column. Two general types of detectors are known in the art: destructive and non-destructive detectors. The destructive detectors perform continuous transformation of the column effluent (burning, evaporation or mixing with reagents) with subsequent measurement of some physical property of the resulting material (plasma, aerosol or reaction mixture). The non-destructive detectors are directly measuring some property of the column eluent (for example UV absorption) and thus affords for the further analysis recovery. Examples of destructive detectors include charged aerosol detector (CAD), flame ionization detector (FID), aerosol-based detector (NQA), flame photometric detector (FPD), atomic-emission detector (AED), nitrogen phosphorus detector (NPD), evaporative light scattering detector (ELSD), mass spectrometer (MS), electrolytic conductivity detector (ELCD), summon detector (SMSD), and mira detector (MD). One example of non-destructive detectors includes UV detectors, including fixed and variable length UV detectors, including diode array detector (DAD) or photodiode array (PDA) detector. UV absorption of the effluent may be measured continuously at single or multiple wavelengths. Other examples of non-destructive detectors include thermal conductivity detector (TCD), fluorescence detector (FLR), electron capture detector, photoionization detector (PID), and refractive index detector (RI or RID). In one example, a DAD/UV detector may be utilized to detect and quantify the eluate material flowing from the column compartment of the system. Bispecific FcFc* antibody, FcFc homodimer, and Fc*Fc* heterodimer selectively elute from the chromatography system, and the signal is picked up by UV detection at 280 nM. Any detector may be adapted to connect a temperature control system, such as temperature controlled flow cells with cooling functions to allow for better stability of protein material.

Figure 5:
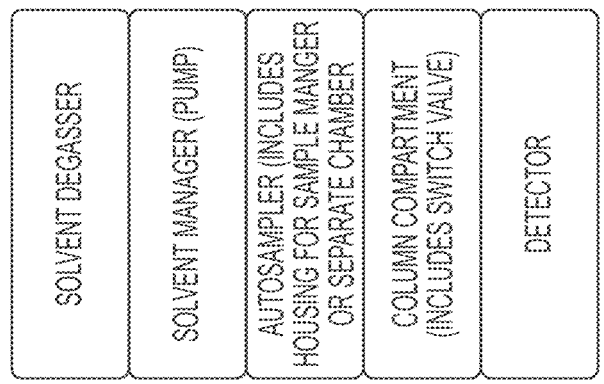
FIG. 5 shows a bispecific antibody titer/purity setup according to an embodiment of the disclosure. The schematic representation depicts a solvent degasser, a solvent manager, a sample manager, a column compartment manager, and a detector.

The present invention may be set up as part of a chromatography system, e.g. a commercially available chromatography system, such as, e.g., an HPLC system available from Shimadzu Corporation, Agilent Technologies, Waters Corporation, or the like. In one non-limiting embodiment, such system comprises, inter alia, a solvent and/or reagent holding unit, a solvent manager/pump, a sample manager, a column compartment manager, and a detector unit. One non-limiting embodiment is depicted in FIG. 5.

The holding unit houses solvents and buffers used in chromatographic applications, and optionally comprises a solvent degasser. In one embodiment, solvents and buffers pass through the solvent degasser prior to flowing to the solvent manager.

The solvent manager is responsible for solvent delivery and may include a computer platform configurable to address the needs of the analytical system according to each particular embodiment in order to improve separation and resolution, and may include, e.g., binary or quaternary gradient modules. The solvent manager may control, inter alia, solvent rates, buffer compositions, and pressure limits of the HPLC system.

The sample manager may optionally comprise a temperature control unit capable of changing the temperature (e.g., cooling and/or heating), or keeping the temperature of the sample constant (by e.g., cooling the sample to a constant temperature) prior to loading onto the columns. In one embodiment, samples are contained in the sample manager compartment and kept at 4° C. while awaiting injection. Samples are brought into the autosampler where a needle goes directly to sample indicated in the queue. In one embodiment, the autosampler further comprises a pressure regulator for handling overflow of injected solvent and/or sample. From the autosampler needle, the sample then moves to the column compartment.

The amount, or quantity, of a protein in a fraction may be determined by eluting the protein through the detector and using computational methods known in the art. The system may further comprise a system controller unit, or other computer-aided device.

The purity and/or quality control analysis is performed by analyzing and quantifying the ratios of the three protein species present in the sample. The purity of a protein in a mixture may be calculated by determining the amount of each protein fraction and calculating the ratio of the amount of the protein of interest to the sum of the amounts of all proteins in the mixture. By way of example, the purity of a heterodimeric protein in a mixture comprising the heterodimeric protein and two or more protein impurities may be quantified by determining the amount of each protein fraction and calculating the ratio of the amount of the heterodimeric protein to the sum of the amounts of the heterodimeric protein and the two or more protein impurities.

The metric bispecific purity gives the percentage of bispecific antibody as compared to total antibody amount, as defined by Equation 1. By way of example, the purity of FcFc* in a mixture comprising FcFc, FcFc*, and Fc*Fc* can be quantified as follows:

$$\text{Quantification of Purity of a Bispecific Antibody Purity of } FcFc^* = \frac{\text{amount of } FcFc^*}{\left(\begin{array}{c}\text{amount of } FcFc + \text{amount of } FcFc^* + \\ \text{amount of } Fc^*Fc^*\end{array}\right)} \quad \text{Equation 1}$$

A switch valve, a flow switch valve, or a flow control valve, as used herein, is a means for directing, varying, or cutting off the flow path of the eluent off a chromatography column. The switch valve may be multi-way, e.g., two-way, three-way, four-way, and the like, i.e. the switch valve is capable of directing the flow to two, three, or more different receptacles. Receptacles may be of any origin, e.g., chromatography columns, affinity chromatography columns, detectors, or a waste disposal bin. The change of the receptacles is achieved by switching the switch valve between different positions.

Figure 4A:
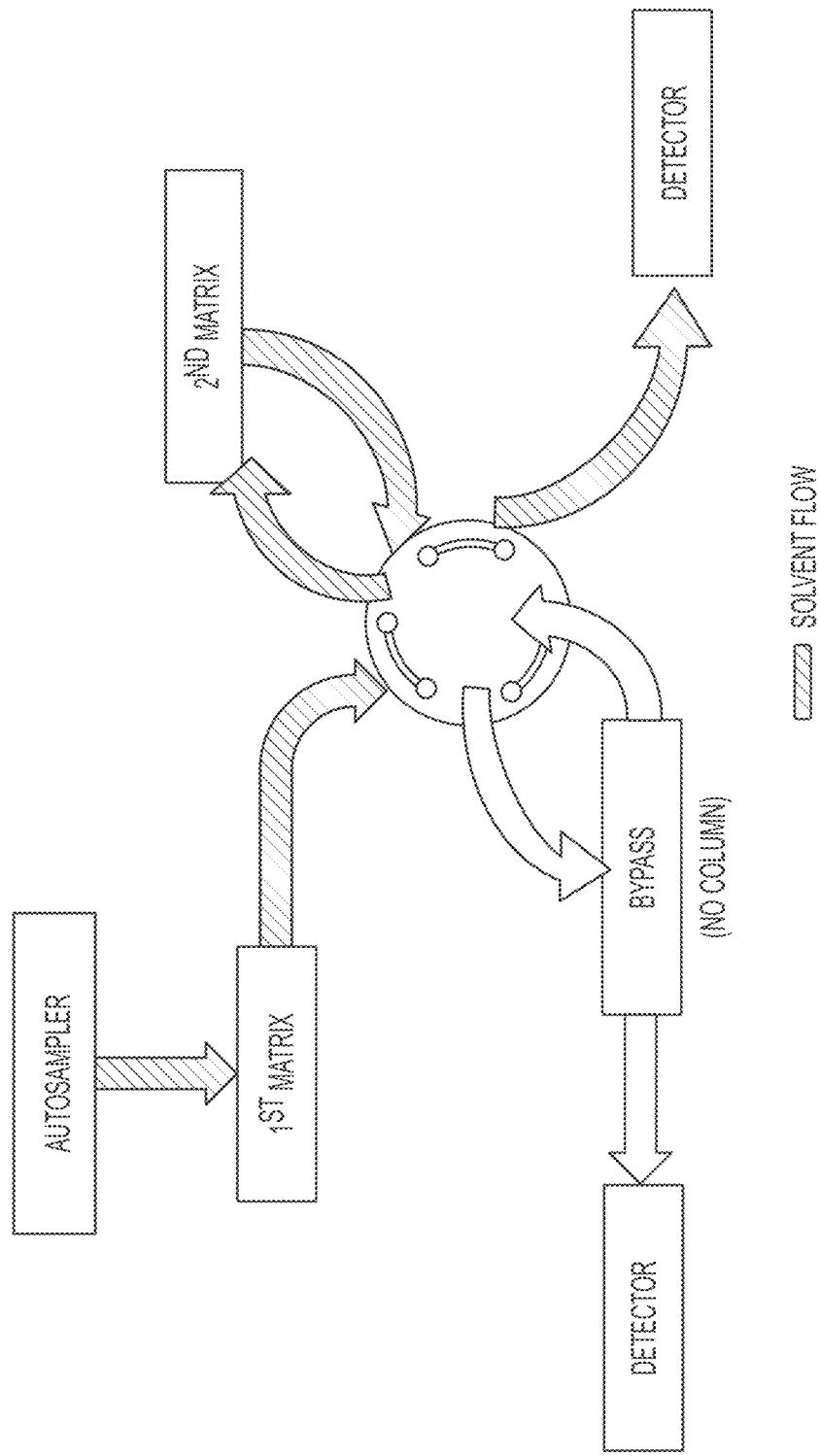
FIGS. 4(A) and 4(B) depict schematic representations of exemplary chromatography systems according to an embodiment of the disclosure. In one exemplary system, shown in FIG. 4(A), an autosampler is connected to a first affinity matrix (column), which is connected to a second affinity matrix (column) and a detector via a switch valve. In the shown configuration, the switch valve is positioned to serially connect the first column with the second column, and the eluent flows through the first column onto the second column, and subsequently through the detector for quantitation. In another exemplary system, shown in FIG. 4(B), an autosampler is connected to a first affinity matrix (column), which is connected to a second affinity matrix (column) via a switch valve. The detector is connected via switch valve in a bypass (no column) configuration. Herein, the switch valve either connects the first column to the second column, which is further connected to the detector, or bypasses the second column and connects the first column directly to the detector.
Figure 4B:
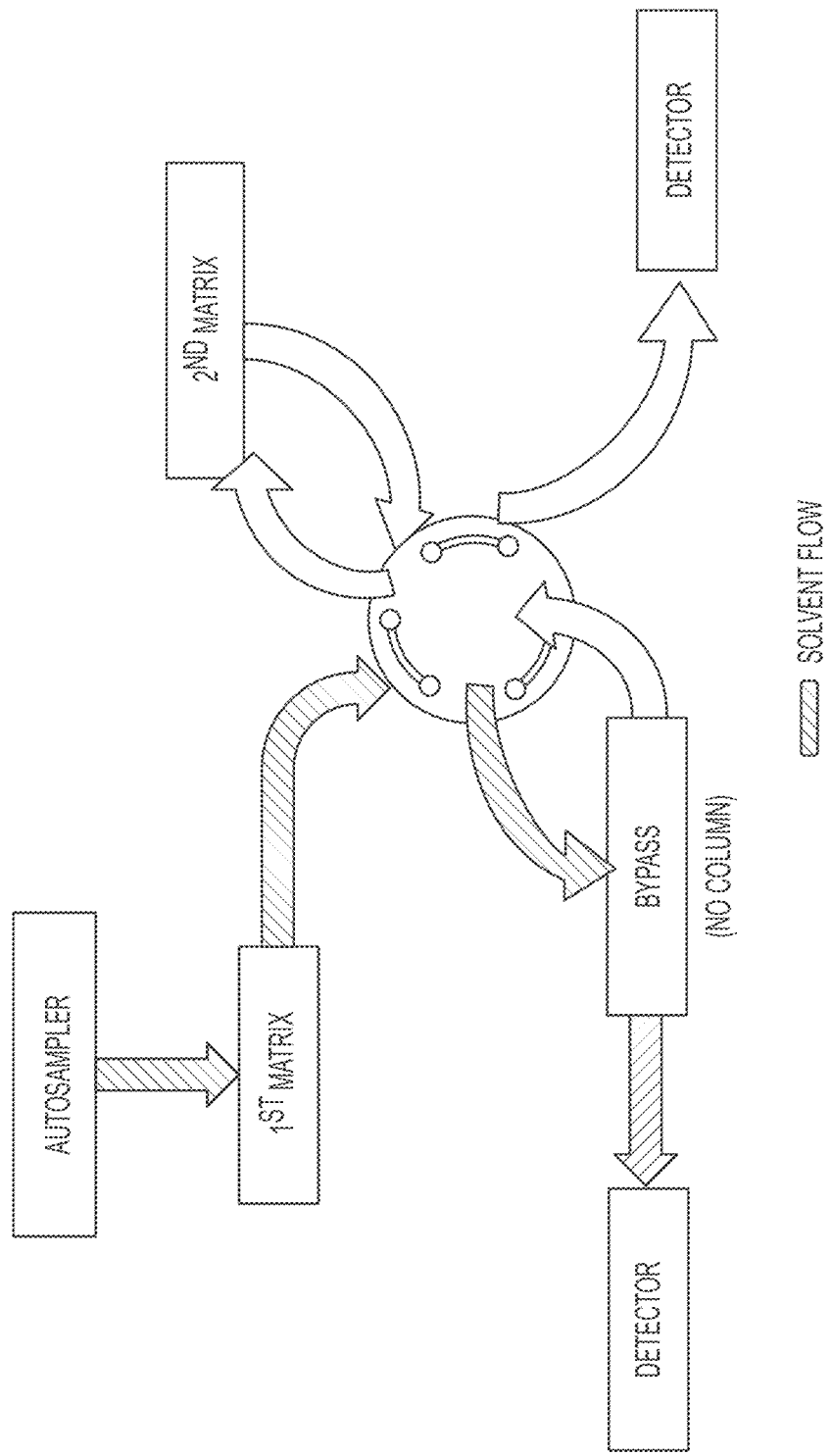
Figure 6:
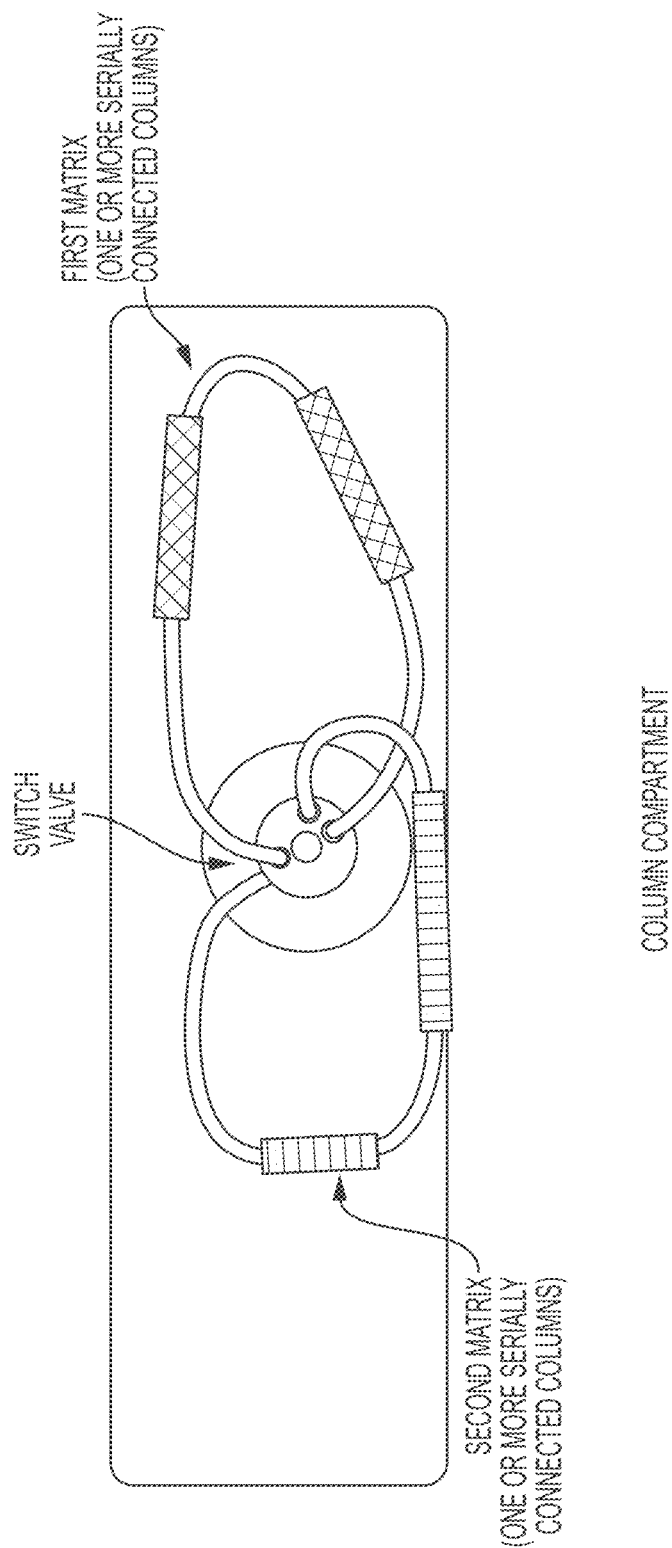
FIG. 6 depicts an exemplary chromatography system according to an embodiment of the disclosure. In this exemplary column compartment of the system, sample moves through to a number of serially connected columns containing the first affinity matrix, followed by a number of serially connected columns containing the second affinity matrix. A switch valve connects first set of columns to the second set of columns.
Figure 7:
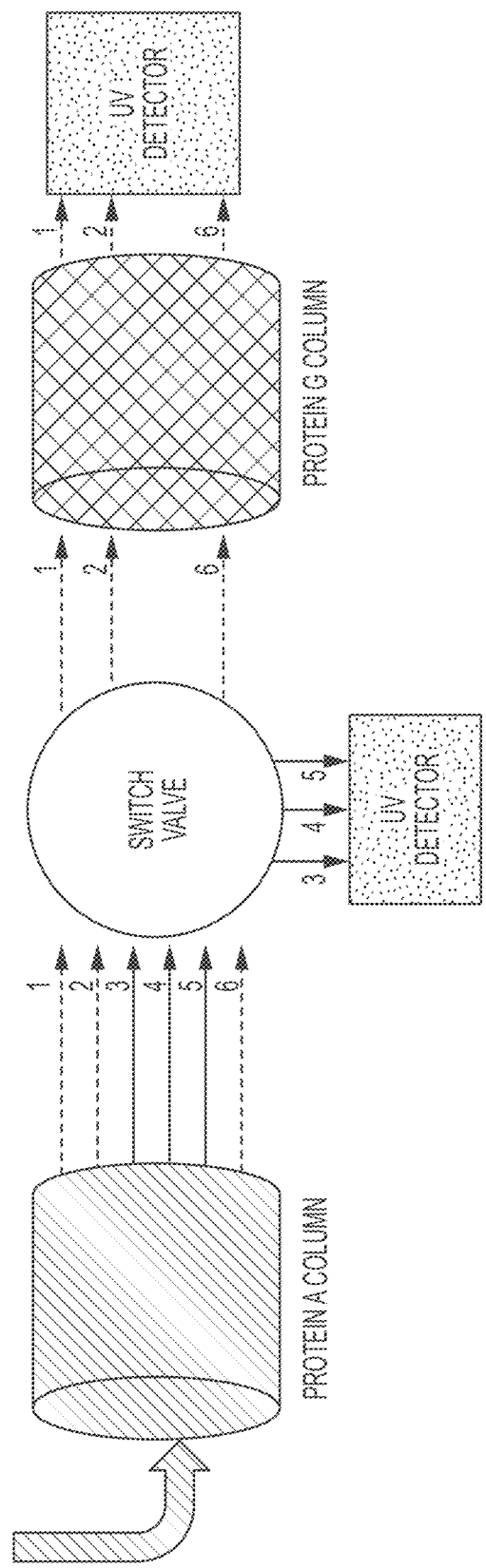
FIG. 7 represents an alternative schematic view of an exemplary chromatography system according to an embodiment of the disclosure.

By way of example, in a chromatography system a switch valve may connect a first affinity matrix, a second affinity matrix, and a detector in a serial or non-serial fashion. In non-limiting embodiments, e.g. shown in FIGS. 5-7, a switch valve may serially connect a first affinity matrix to a second affinity matrix. In this exemplary system, one switch valve position would allow the eluent to flow from the first affinity matrix to the second affinity matrix and, subsequently, to the detector. Switching the switch valve to another position would allow the eluent to flow from the first affinity matrix directly to the detector, bypassing the second affinity matrix. The eluent from the second affinity matrix may flow to the detector with or without engaging the first affinity matrix. The second affinity matrix may or may not be directly connected to an autosampler. In another non-limiting embodiment depicted in FIG. 4B, the eluent from the first affinity matrix is able to flow directly to the detector, bypassing the second affinity matrix.

In one aspect, the present invention describes a method of quantitatively assessing the amount and/or purity of the heterodimer fraction by utilizing a novel chromatography system comprising a switch valve.

In one aspect, the present invention describes a method for quantifying an amount and/or purity of a protein in a sample comprising a mixture of the protein, a first protein impurity, and a second protein impurity, wherein the protein and the first impurity bind to a first affinity matrix and the second impurity does not substantially bind to the first affinity matrix and binds to a second affinity matrix, said method comprising the steps of:

a. applying the sample to a chromatography system comprising the first affinity matrix, the second affinity matrix, and a detector, wherein the first affinity matrix is serially connected to the second affinity matrix via a switch valve;

b. eluting the second impurity from the first affinity matrix onto the second affinity matrix under a first set of conditions;

c. switching the switch valve to bypass the second affinity matrix, eluting the protein through the detector under a second set of conditions, and determining the amount of the eluted protein;

d. eluting the first impurity through the detector under a third set of conditions and determining the amount of the eluted first impurity;

e. eluting the second impurity from the second affinity matrix through the detector under the third set of conditions, and determining the amount of the eluted second impurity, and
f. quantifying the amount and/or purity of the protein in the sample.

In one embodiment the protein is a multimeric protein, e.g. an antibody. In one embodiment, the protein is an antibody of interest, and the first and second protein impurities are multimeric proteins, e.g., antibodies that may or may not be structurally related to the antibody of interest. In one embodiment, the protein is a bispecific antibody, i.e., a heterodimeric protein, the first protein impurity is a first homodimeric protein, and the second protein impurity is a second homodimeric protein. In some cases, the mixture of multimeric proteins is produced by a plurality of eukaryotic cells, such as, for example, Chinese hamster ovary (CHO) cells in a cell culture.

In one embodiment, the protein has a lower affinity to the first affinity matrix than the first impurity. In one embodiment the protein is a heterodimeric protein, the first protein impurity is a first homodimeric protein, and the second protein impurity is a second homodimeric protein, the heterodimeric protein and the first homodimeric protein bind to the first affinity matrix and the second homodimeric protein does not substantially bind to the first affinity matrix and binds to the second affinity matrix.

In one embodiment, the protein comprises a first immunoglobulin CH3 domain and a second immunoglobulin CH3 domain, wherein said first and second immunoglobulin CH3 domains are different in their affinity to the first affinity matrix, and wherein the sample comprises a mixture comprising said protein, a protein comprising two first CH3 domains, and a protein comprising two second CH3 domains.

In one embodiment, the second CH3 domain comprises H435R and Y436F (by EU numbering system; H95R/Y96F by IMGT exon numbering system) amino acid substitutions.

In one embodiment, the first affinity matrix comprises a protein A ligand and its derivatives affixed to a solid substrate. In some cases, the substrate is a bead or particle, such that the affinity matrix is a plurality of particles affixed with Protein A. The Protein A may be a naturally occurring or modified Staphylococcal Protein A, or it may be an engineered Protein A. Engineered Protein A may be for example a Z-domain tetramer, a Y-domain tetramer, or an engineered Protein A that lacks D and E domains. These engineered Protein A exemplars are unable to bind (or bind with very low affinity if at all) to the VH3 domain of an immunoglobulin, but can still bind to the CH3 domains of IgG1, IgG2 and IgG4.

In one embodiment, the second affinity matrix comprises a protein G ligand and its derivatives affixed to a solid substrate. In some cases, the substrate is a bead or particle, such that the affinity matrix is a plurality of particles affixed with Protein G. The Protein G may be a naturally occurring or modified Streptococcal Protein G, or it may be an engineered Protein G. Engineered Protein G may comprise the B1 domain (aka GB1) and may be conjugated or unconjugated. In another embodiment, the second affinity matrix comprises a protein L ligand and its derivatives affixed to a solid substrate.

In one embodiment, elution conditions may comprise a particular pH range and a buffer comprising a mobile phase modifier, e.g., a chaotropic agent. In one embodiment, the first set of elution conditions for eluting the second impurity, e.g., the second homodimeric protein, comprises a first pH.

In one embodiment, the second set of elution conditions for eluting the protein, e.g., the heterodimeric protein, comprises a second pH. In one embodiment, the third set of elution conditions for eluting the first impurity, e.g., the first homodimeric protein, comprises a third pH. In one embodiment, the second pH may be lower than the first pH. In one embodiment, the third pH may be lower than the second pH. In one embodiment, the second pH may be lower than the first pH, and the third pH may be lower than the second pH. In another embodiment, the first pH may be greater than pH 5, or about pH 5 to about pH 8, or about pH 5.2 to about pH 7.4, or pH 6.4. In one embodiment, the second pH may be about pH 3.5 to about pH 6, or about 3.8 to about 5.6. In one embodiment, the third pH may be less than pH 4, or about pH 1.5 to about pH 3.6, or about pH 2.0 to about pH 2.8, or about pH 2.2.

In one embodiment, the first, second, and third sets of elution conditions comprise a suitable buffer, e.g., a citrate, acetate, 4-Morpholineethanesulfonate (MES), phosphate, succinate, and the likes, as well as combinations and mixtures thereof. In one embodiment, the first, second, and third sets of elution conditions comprise a chaotropic agent. The chaotropic agent can be a salt, having a cation selected from lithium, magnesium, calcium, and guanidinium, and an anion selected from chloride, nitrate, bromide, chlorate, iodide, perchlorate, and thiocyanate. In one particular embodiment, the chaotropic agent is $CaCl_2$, for example 250-500 mM $CaCl_2$. In another particular embodiment, the chaotropic agent is $MgCl_2$, for example 250-500 mM $MgCl_2$.

In one embodiment, the heterodimer is a bispecific antibody. Here, the first polypeptide comprises a CH3 domain that is capable of binding to Protein A ("Fc") and the second polypeptide comprises a CH3 domain that is not capable of binding to Protein A ("Fc*"). In some cases, the second polypeptide comprises a H435R/Y436F (by EU numbering system; H95R/Y96F by IMGT exon numbering system) substitution in its CH3 domain (a.k.a "Fc*" or "star substitution"). Thus, in some embodiments, the first homodimer is a monospecific antibody having two unsubstituted CH3 domains (i.e., FcFc); the second homodimer is a monospecific antibody having two H435R/Y436F substituted CH3 domains (i.e., Fc*Fc*); and the heterodimer is a bispecific antibody having one unsubstituted CH3 domain and one H435R/Y436F substituted CH3 domain (i.e., Fc*Fc).

In another aspect, the present invention describes a method for quantifying an amount and/or purity of a heterodimeric protein in a sample comprising a mixture of the heterodimeric protein, a first homodimeric protein, and a second homodimeric protein, wherein the heterodimeric protein and the first homodimeric protein bind to a protein A matrix and the second homodimeric protein does not substantially bind to the protein A matrix and binds to a protein G matrix, said method comprising the steps of:
  a. applying the sample to a chromatography system comprising the protein A matrix, the protein G matrix, and a detector, wherein the protein A matrix is serially connected to the protein G matrix via a switch valve;
  b. eluting the second homodimeric protein from the protein A matrix onto the protein G matrix under a first set of conditions;
  c. switching the switch valve to bypass the protein G matrix, eluting the heterodimeric protein through the detector under a second set of conditions, and determining the amount of the eluted protein;

d. eluting the first homodimeric protein through the detector under a third set of conditions and determining the amount of the eluted first impurity;

e. eluting the second homodimeric protein from the second affinity matrix through the detector under the third set of conditions, and determining the amount of the eluted second impurity, and f. quantifying the amount and/or purity of the protein in the sample.

Differential binding of the first homodimer and the heterodimer to the second affinity matrix can be manipulated by changing inter alia the pH and/or ionic strength of a solution that is passed over the affinity matrix. The addition of a chaotropic agent to the solution enhances the elution each dimer species from the second affinity matrix in non-overlapping fractions, thereby increasing to purity of each dimer species. In one embodiment, the first homodimer, e.g. Fc*Fc*, is eluted from the first affinity matrix onto the second affinity matrix in a buffer having a first pH. In one embodiment, the heterodimer, e.g. the FcFc* heterodimer, is eluted from the first affinity matrix bypassing the second affinity matrix directly to the detector in a buffer having a second pH range. In one embodiment, the second homodimer, e.g. FcFc is eluted from the first affinity matrix bypassing the second affinity matrix directly to the detector in a buffer having a third pH range. In one embodiment, the first homodimer, e.g. Fc*Fc*, is eluted from the second affinity matrix onto the detector in a buffer having a third pH. Here, the first pH range comprises a higher pH than does the second pH range, and the second pH range comprises a higher pH than does the third pH range.

In one embodiment, the first set of elution conditions for eluting the second impurity, e.g., the second homodimeric protein, comprises a first pH. In one embodiment, the second set of elution conditions for eluting the protein, e.g., the heterodimeric protein, comprises a second pH. In one embodiment, the third set of elution conditions for eluting the first impurity, e.g., the first homodimeric protein, comprises a third pH. In one embodiment, the second pH may be lower than the first pH. In one embodiment, the third pH may be lower than the second pH. In one embodiment, the second pH may be lower than the first pH, and the third pH may be lower than the second pH. In another embodiment, the first pH may be greater than pH 5, or about pH 5 to about pH 8, or about pH 5.2 to about pH 7.4. In one embodiment, the second pH may be about pH 4 to about pH 5, or about 4.2 to about 5.0. In one embodiment, the third pH may be less than pH 4, or about pH 2 to about pH 3.6, or about pH 2.2 to about pH 2.8.

In one aspect, a method for determining a quantity and/or purity of a FcFc* protein in a sample is disclosed, wherein said FcFc* protein comprises a first immunoglobulin CH3 domain (Fc), a fragment and/or a derivative thereof, and a second immunoglobulin CH3 domain (Fc*), a fragment and/or a derivative thereof, wherein said first and second immunoglobulin CH3 domains are different in their affinity to a first protein affinity matrix, and wherein the sample comprises a mixture comprising said FcFc* protein, a protein comprising two first CH3 domains (FcFc protein), and a protein comprising two second CH3 domains (Fc*Fc* protein), said method comprising the steps of:

(a) applying the sample to the first protein affinity matrix under a first set of conditions, wherein said FcFc* protein and said FcFc protein bind to said first protein affinity matrix and said Fc*Fc* protein does not substantially bind to said first protein affinity matrix;

(b) washing said first protein affinity matrix under the first set of conditions;

(c) applying the flow-through from step (a) and the wash from step (b) to a second protein affinity matrix under such set of conditions that the Fc*Fc* protein binds to said second protein affinity matrix;

(d) washing said second protein affinity matrix under the same set of conditions as in step (c);

(e) eluting the Fc*Fc* protein from said second protein affinity matrix and determining the amount of said eluted Fc*Fc* protein;

(f) eluting the remaining bound Fc*Fc* protein from said first protein affinity matrix under a second set of conditions, and determining the amount of said eluted Fc*Fc* protein;

(g) eluting the FcFc* protein bound to said first protein affinity matrix under a third set of conditions, and determining the amount of said eluted FcFc* protein;

(h) eluting the FcFc protein bound to said first protein affinity matrix under a fourth set of conditions, and determining the amount of said eluted FcFc protein, and (i) determining the quantity and/or purity of the FcFc* protein in the sample, wherein step (d) and/or step (e) can be performed simultaneously with, before or after steps (f)-(h).

In one aspect, a method for determining a quantity and/or purity of a bispecific antibody (e.g., an FcFc* antibody) in a sample is disclosed, wherein said FcFc* antibody comprises a first immunoglobulin heavy chain (Fc) and a second immunoglobulin heavy chain (Fc*) wherein said first and second immunoglobulin heavy chains are different in their affinity to protein A, and wherein the sample comprises a mixture comprising said FcFc* antibody, an antibody comprising two first heavy chains (FcFc antibody), and an antibody comprising two second heavy chains (Fc*Fc* antibody), said method comprising the steps of:

(a) applying the sample to a protein A affinity column (protein A column) under a first set of conditions, wherein said FcFc* antibody and said FcFc antibody bind to said protein A column, while said Fc*Fc* antibody does not substantially bind to said protein A column, and wherein the protein A column is connected through a switch valve to a protein G affinity column (protein G column) so that the flow-through from the protein A column can be directly applied to the protein G column, which protein G column is further connected to an HPLC column;

(b) washing said protein A column under the first set of conditions with the switch valve in a position so that the flow-through from the protein A column is directly applied to the protein G column;

(c) washing the protein G column under the same conditions as in step (b);

(d) eluting the Fc*Fc* antibody from the protein G column and determining the amount of said eluted Fc*Fc* antibody;

(e) putting the switch valve in the position disconnecting the protein A column from the protein G column and connecting said protein A column with an HPLC column;

(f) eluting the remaining bound Fc*Fc* antibody from the protein A column under a second set of conditions, and determining the amount of said eluted Fc*Fc* antibody using;

(g) eluting the FcFc* antibody bound to said protein A column under a third set of conditions, and determining the amount of said eluted FcFc* antibody;

(h) eluting the FcFc antibody bound to said protein A column under a fourth set of conditions, and determining the amount of said eluted FcFc antibody, and (i) determining the quantity and/or purity of the FcFc* protein in the sample, wherein step (c) and/or step (d) can be performed simultaneously with, before or after steps (e)-(h).

In another aspect, a chromatography system for purifying, analyzing, and/or assessing amount and/or purity of proteins is provided. In one embodiment, the chromatography system comprises a first affinity matrix, a second affinity matrix, and a detector, wherein each of the first affinity matrix, the second affinity matrix and the detector are connected via a switch valve. In one embodiment, the first affinity matrix may be a protein A chromatography column. In one embodiment, a second affinity matrix may be a protein G or a protein L chromatography column.

In one embodiment, the detector may be an HPLC column equipped with a UV detector, a charge aerosol detector, and/or a mass-spectrometer. In one embodiment, the first affinity matrix and the second affinity matrix are serially connected via a switch valve. In another embodiment, the first affinity matrix, the second affinity matrix, and the detector are all serially connected via a switch valve. In one embodiment, the first affinity matrix and the second affinity matrix are serially connected via a switch valve, but the detector is non-serially connected to the first affinity matrix and the second affinity matrix.

In one embodiment, a chromatography system is provided comprising (i) a protein A chromatography column, (ii) a protein G chromatography column, and (iii) a detector comprising an HPLC column equipped with a UV detector, a charge aerosol detector, and/or a mass-spectrometer, wherein each of the protein A chromatography column, the protein G chromatography column and to the detector are connected via a switch valve.

EXAMPLES

The following examples illustrate specific aspects of the instant description. The examples should not be construed as limiting, as the examples merely provide specific understanding and practice of the embodiments and their various aspects.

Chromatograpy experiments were performed using an HPLC system, adapted to the configurations needed to perform the method described herein. InfinityLab Quick Change valves are available from Agilent Technologies. Examples of suitable valves include, but are not limited to, Agilent Quick Change Valve G4231A/C, G4232C/D, G4234A/C, G4236A/B, and G4238A/B. Non-limiting examples of valves suitable for practicing the invention is provided at world wide web agilent.com/cs/library/user-manuals/public/G4232-90009_ValveKit_TN_EN.pdf, and also Acquity UPLC Systems with 2D Technology Capabilities Guide, Revision A, Waters Corporation, 2012, each of which is incorporated by reference herein in its entirety.

Example 1

The purity and quantity of a bispecific antibody in a mixture comprising two contaminating homodimers was determined as follows (titer chromatogram is depicted as FIG. 1). Two heavy chain polypeptides (IgG4 Fc- and IgG4-Fc*-containing) and a common light chain polypeptide were co-expressed in CHO cells. A sample of the cell supernatant comprising the resulting mixture of homodimers and heterodimer was subjected to high-speed centrifugation to eliminate protein aggregates, and the supernatant was subjected to affinity chromatography according to purification methods described in PCT Publication No. WO2016/018740, published Feb. 4, 2016, hereby incorporated by reference. A sample of the purification product, containing FcFc* heterodimer and any impurity products, FcFc and Fc*Fc* homodimers, were loaded onto a 3×0.1 mL POROS® A 20 µm Protein A column (rProA, obtained from Applied Biosystems, #2-1001-00) in pH 6.4 mobile phase containing 0.5 M NaCl. The Protein A column was serially connected to a 2×0.1 mL POROS® G 20 µm Protein G column (rProG, obtained from Applied Biosystems, #2-1002-00) and to a standard UV detector (2.0 mL/min flow rate, UV@280 nm peak detection) via a switch valve as outlined in FIG. 4A.

A series of washes was applied to remove process-related contaminants such as CHO DNA or host cell protein (HCP). The mixture was eluted using pH 5.6 mobile phase containing 0.5M $CaCl_2$. Since Fc*Fc* homodimer has both Protein A binding sites deleted from the Fc region, this product-related impurity was expected to flow though the rProA onto the rProG, while the bispecific FcFc* and FcFc homodimer was expected to be retained on the rProA.

The switch valve was then switched to take rProG offline, connecting rProA directly to the detector. The bispecific FcFc* antibody was then selectively eluted from rProA at to the detector using pH 3.8-5.6 (molecule specific) mobile phase containing 0.5M calcium chloride, while the FcFc impurity was retained due to its stronger binding relative to the bispecific FcFc* antibody. The amount of FcFc* was calculated. Then, the FcFc impurity was selectively eluted from rProA using pH 2.2 mobile phase containing 0.5M calcium chloride to the detector, and the amount of FcFc was calculated.

The switch valve was then switched back to serially connect rProG online, connecting rProA to rProG, and rProG to the detector. The Fc*Fc* impurity was then eluted using pH 2.2 mobile phase containing 0.5M calcium chloride to the detector, and the amount of Fc*Fc* was calculated.

The amount and purity of FcFc* bispecific antibody was determined by calculating the ratio of the FcFc* fraction to the sum of the FcFc, FcFc*, and Fc*Fc* fractions.

Method flow rate, wash length, bispecific elution length, and % Buffer C in the elution step of the method were continuous factors that were studied and deemed probable to have an effect on the recovery of all three antibody species. Table 1, below, shows the parameters, their role, and the values studied in the method.

TABLE 1

| Bispecific Purity Robustness Factors | | |
|---|---|---|
| Name | Role | Values |
| Load Flow Rate (mL/min) | Continuous | 0.5-2.5 |
| Wash Length (CV) | Continuous | 0-60 |
| Bispecific Elution Length (CV) | Continuous | 10-130 |
| % C | Continuous | 5-30 |
| Isotype | Categorical | IgG1*, IgG4*A, IgG4*B |

Table 2, below, shows the various sets of run conditions for the inventive methods of assessing purity and quantity of three antibody samples: IgG*1, IgG4*A and IgG4*B.

TABLE 2

Bispecific Purity Robustness Run Conditions

| Condition # | Flow Rate (mL/min) | Wash Length (CV) | Bispecific Elution Length (CV) | % Buffer C | Isotype |
|---|---|---|---|---|---|
| 1 | 0.5 | 0 | 10 | 5 | IgG1* |
| 2 | 0.5 | 0 | 10 | 17.5 | IgG4* B |
| 3 | 0.5 | 0 | 10 | 30 | IgG4* A |
| 4 | 0.5 | 0 | 130 | 5 | IgG4* A |
| 5 | 0.5 | 0 | 130 | 30 | IgG1* |
| 6 | 0.5 | 30 | 130 | 5 | IgG4* B |
| 7 | 0.5 | 60 | 10 | 5 | IgG4* A |
| 8 | 0.5 | 60 | 10 | 30 | IgG1* |
| 9 | 0.5 | 60 | 70 | 30 | IgG4* B |
| 10 | 0.5 | 60 | 130 | 5 | IgG1* |
| 11 | 0.5 | 60 | 130 | 30 | IgG4* A |
| 12 | 1.5 | 0 | 130 | 30 | IgG4* B |
| 13 | 1.5 | 30 | 10 | 5 | IgG4* B |
| 14 | 1.5 | 30 | 70 | 17.5 | IgG4* A |
| 15 | 1.5 | 60 | 130 | 5 | IgG4* B |
| 16 | 2.5 | 0 | 10 | 5 | IgG4* A |
| 17 | 2.5 | 0 | 10 | 30 | IgG1* |
| 18 | 2.5 | 0 | 70 | 5 | IgG4* B |
| 19 | 2.5 | 0 | 130 | 5 | IgG1* |
| 20 | 2.5 | 0 | 130 | 30 | IgG4* A |
| 21 | 2.5 | 30 | 10 | 30 | IgG4* B |
| 22 | 2.5 | 30 | 130 | 17.5 | IgG4* B |
| 23 | 2.5 | 60 | 10 | 5 | IgG1* |
| 24 | 2.5 | 60 | 10 | 17.5 | IgG4* B |
| 25 | 2.5 | 60 | 10 | 30 | IgG4* A |
| 26 | 2.5 | 60 | 130 | 5 | IgG4* A |
| 27 | 2.5 | 60 | 130 | 30 | IgG1* |

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings. Accordingly, the present description is intended to embrace all such alternatives, modifications, and variances which fall within the scope of the appended claims.

All patents, applications, publications, test methods, literature, and other materials cited herein are hereby incorporated by reference in their entirety as if physically present in this specification.

What is claimed is:

1. A method for quantifying an amount and purity of a heterodimeric antibody in a sample comprising a mixture of the heterodimeric antibody, a first homodimeric antibody impurity, and a second homodimeric antibody impurity, wherein the heterodimeric antibody and the first homodimeric antibody impurity bind to a first affinity matrix and the second homodimeric antibody impurity does not substantially bind to the first affinity matrix and binds to a second affinity matrix, and wherein the heterodimeric antibody has a lower affinity to the first affinity matrix than the first homodimeric antibody impurity,
    wherein the heterodimeric antibody is a bispecific human IgG1, IgG2, or IgG4 antibody having one unsubstituted CH3 domain and one H435R/Y436F substituted CH3 domain (FcFc* antibody), H435R/Y436F is by the European Union (EU) numbering system, the first homodimeric antibody impurity is a monospecific human IgG1, IgG2, or IgG4 antibody comprising two unsubstituted CH3 domains (FcFc antibody), and the second homodimeric antibody impurity is a monospecific human IgG1, IgG2, or IgG4 antibody comprising two substituted CH3 domains (Fc*Fc* antibody), wherein the first affinity matrix comprises protein A (protein A affinity matrix) and the second affinity matrix comprises protein G (protein G affinity matrix), wherein the unsubstituted CH3 domain binds to both protein A affinity matrix and protein G affinity matrix, the H435R/Y436F substituted CH3 domain binds to protein G affinity matrix but does not substantially bind to protein A affinity matrix, and wherein Fc denotes a heavy chain having the unsubstituted CH3 domain and Fc* denotes a heavy chain having the H435R/Y436F substituted CH3 domain;
said method comprising the steps of:
(a) applying the sample to the protein A affinity matrix in a chromatography system under conditions wherein the FcFc* antibody and the FcFc antibody bind to the protein A affinity matrix, wherein the chromatography system comprises the protein A_affinity matrix, the protein G affinity matrix, a switch valve, and a detector, wherein the protein A affinity matrix is serially connected to the protein G affinity matrix via the switch valve;
(b) washing the protein A affinity matrix after step (a) under a first set of conditions with the switch valve in a position so that the flow-through is directly applied onto the protein G affinity matrix such that the Fc*Fc* antibody in the flow-through binds to the protein G affinity matrix;
(c) switching the switch valve after step (b) to disconnect the protein A affinity matrix from the protein G affinity matrix and to connect the protein A affinity matrix directly to the detector, and then eluting the FcFc* antibody from the protein A affinity matrix through the detector under a second set of conditions while the FcFc antibody is retained, and determining the amount of the eluted heterodimeric FcFc* antibody;
(d) after the step (c), eluting the retained FcFc antibody from the protein A affinity matrix through the detector under a third set of conditions and determining the amount of the eluted FcFc antibody;
(e) after step (d), switching the switch valve back to serially connect the protein A affinity matrix to the protein G affinity matrix and the protein G affinity matrix to the detector and then eluting the Fc*Fc* antibody through the detector under the third set of conditions, and determining the amount of the eluted Fc*Fc* antibody, and
(f) quantifying the amount of the heterodimeric FcFc* antibody in the sample as in step (c) and the purity of the heterodimeric antibody in the sample, wherein
the purity of the heterodimeric antibody is determined by the ratio of the amount of the FcFc* antibody to the sum of the amounts of the FcFc antibody, the FcFc* antibody, and the Fc*Fc* antibody.

2. The method of claim 1, wherein the first set of conditions comprises a first pH, the second set of conditions comprises the second pH, and the third set of conditions comprises a third pH.

3. The method of claim 2, wherein the second pH is lower than the first pH, and the third pH is lower than the second pH.

4. The method of claim 2, wherein the first pH is from about pH 5.0 to about pH 7.4, the second pH is from about pH 4.3 to about pH 5.6 and the third pH is from about pH 2.0 to about pH 2.8.

5. The method of claim 1, wherein the first set of conditions, the second set of conditions, and the third set of conditions comprise a mobile phase modifier.

6. The method of claim 5, wherein the mobile phase modifier is a salt buffer selected from LiCl, NaCl, KCl, $MgCl_2$, and $CaCl_2$ buffer.

* * * * *